United States Patent [19]

Russell et al.

[11] 4,331,136
[45] May 25, 1982

[54] LIGHT SHIELD

[75] Inventors: Frederick L. Russell, Charlottesville; Charles M. Davis, Albemarle County, both of Va.

[73] Assignee: Maximate Limited Partnership, Keswick, Va.

[21] Appl. No.: 131,002

[22] Filed: Mar. 17, 1980

[51] Int. Cl.³ ............................................. A61F 13/12
[52] U.S. Cl. .................................................... 128/163
[58] Field of Search ................... 128/1 C, 132 R, 133, 128/149, 163, 155, 249, 154, 97; 2/9, 15, 426

[56] References Cited

U.S. PATENT DOCUMENTS

| | | | |
|---|---|---|---|
| 1,917,117 | 7/1933 | Hines | 128/163 |
| 1,924,315 | 8/1933 | Hemphill et al. | 128/163 |
| 2,675,001 | 4/1954 | Jones | 128/283 |
| 3,068,863 | 12/1962 | Bowman | 128/132 R |
| 3,092,103 | 6/1963 | Mower | 128/132 R |
| 3,521,630 | 7/1970 | Westberg et al. | 128/206.15 |
| 3,952,727 | 4/1976 | Nolan | 128/283 |
| 3,952,735 | 4/1976 | Wirtschafter | 128/132 R |
| 4,120,715 | 10/1978 | Ockwell et al. | 128/283 |
| 4,122,847 | 10/1978 | Craig | 128/132 R |

FOREIGN PATENT DOCUMENTS

| | | | |
|---|---|---|---|
| 7606486 | 12/1977 | Netherlands | 2/15 |
| 1376888 | 12/1974 | United Kingdom | 128/205.17 |

Primary Examiner—John D. Yasko
Attorney, Agent, or Firm—LeBlanc, Nolan, Shur & Nies

[57] ABSTRACT

A shield which keeps light from reaching a subject's eyes. The shield is permeable, but capable of blocking the transmission of light; and it has an adhesive for removably securing it to the user's face. An accessory usable with the mask to extend its useful life by replacing the shield securing adhesive is also disclosed.

4 Claims, 8 Drawing Figures

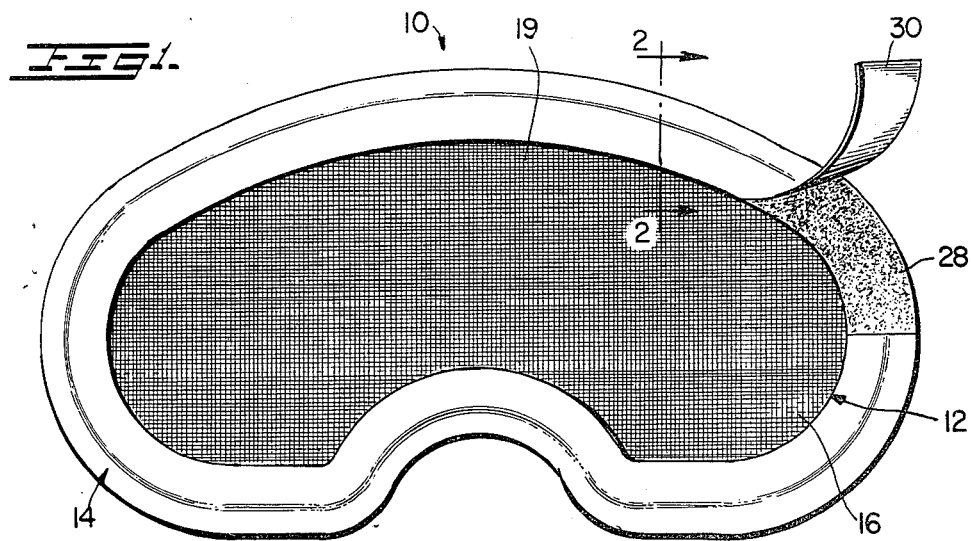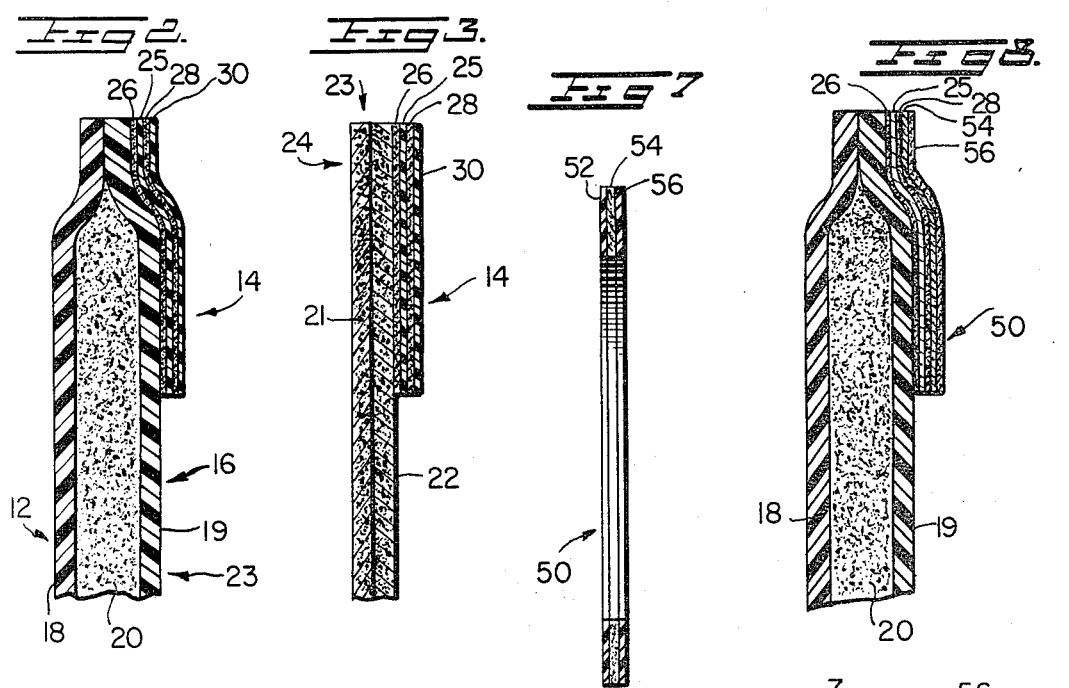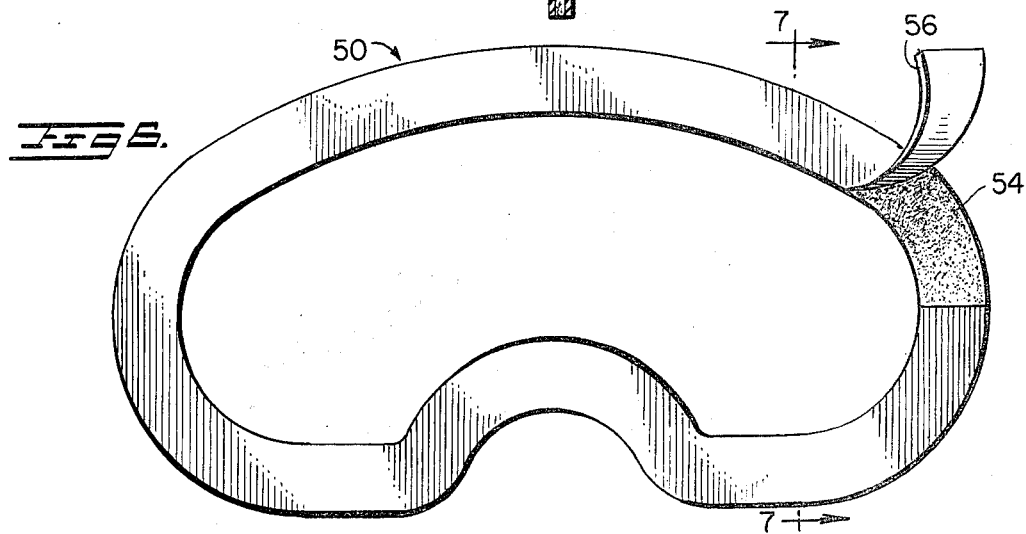

LIGHT SHIELD

This invention relates to light shields and, more particularly, to novel devices of that character which keep light from reaching the user's eyes while allowing air to circulate to those facial regions masked by the shield.

Human applications of our invention are particularly important at present, and the principles of our invention will accordingly be developed primarily by reference to such applications. It is to be understood, however, that this is being done primarily for convenience and clarity and is not intended to limit the scope of the appended claims as the principles of our invention can readily be embodied in shields which are useful in other purposes; e.g., in treating bovine animals for pink eye.

One particularly important application in which our invention can be employed to advantage is in helping humans (and potentially other animals) to reach their full growth potential. It is well-known that infants and adolescents grow in spurts, and it now appears that sufficient sleep may be one of the prime factors in ensuring that maximum growth is realized in these spurts.

Sleep in total darkness is the most efficient in promoting growth. Under most conditions the attainment of this goal dictates artificial aid. Human eyelids transmit approximately three percent of the light impinging on them; and, because of the extraordinary sensitivity of the photoreceptors in the human eye, this is far more than enough to adversely affect the quality of sleep.

Shields or masks designed to keep light from a subject's eyes have heretofore been developed although not for the purposes discussed above. For the most part these prior art devices, such as the conventional eye patch, are secured to the subject's face by a strap, headband, or similar arrangement. They are relatively ineffective in circumstances calling for total darkness because they can shift during use and because of their design, which has in no case known to us been directed to the complete prevention of light transmission.

Because of the foregoing, light can penetrate to the wearer's eyes, directly around the edges of the shield and through the soft tissue surrounding (or overlying) the eyes. Because of the extreme sensitivity of the photoreceptors alluded to above, this can adversely affect the gains sought by blocking the transmission of light to the subject's eyes.

Furthermore, previously proposed eye shields and protective devices tend to become uncomfortable after having been worn for a time. This disadvantage is generally attributable to a build-up of moisture behind the shield and an amassing of odors and to the bands, straps, or other harnesses typically employed to retain such shields in place and the rigid, inflexible construction of such shields.

We have now invented a novel light shield which is capable of totally blocking the transmission of light to the eyes of the subject or user of the shield. This is an important advance particularly in applications such as that discussed above where total darkness is a paramount goal.

Also, our novel light shields are comfortable over extended periods. They are soft and pliable; and they can be attached to the subject's face without bands, straps, or other harnesses. Furthermore, our novel shields allow air to circulate freely to the subject's face; and they absorb moisture and odors, further contributing to the user's comfort.

The foregoing and other important advantages are obtained by a novel laminate construction which makes the shield opaque but allows air to circulate freely through it. Odor and moisture absorbing materials are employed in this laminate construction which is soft and pliable.

Our novel light shields are furthermore so dimensioned and configured that light cannot penetrate through soft tissue to the user's eyes when they are in place.

They are attached to the subject's face and kept from shifting even during the movements which occur during sleep, for example, by a band of adhesive around the periphery of the shield. This, because the softness and pliability of our shields permits them to conform accurately to the contours of the subject's face, also results in a tight seal which keeps light from leaking past the edges of the shield to the user's eyes.

The adhesive mode of attachment also contributes to the user's comfort by eliminating the bands, straps, etc. heretofore employed to keep light shields in place.

We point out, in conjunction with the foregoing, that the use of an adhesive to attach eye patches and other protective devices to a user's face has heretofore been proposed as evidenced by U.S. Pat. Nos. 3,068,863 issued Dec. 18, 1962, to Bowman; 3,092,103 issued June 4, 1963, to Mower; 3,952,735 issued Apr. 27, 1976, to Wirtschafter et al; and 4,122,847 issued Oct. 31, 1978, to Craig. Otherwise, however, the protective devices disclosed in the foregoing patents bear little resemblance to our novel light shields. They are not configured or otherwise constructed in a manner which would completely block the transmission of light to a subject's eyes as ours do; and they lack the features we employ to ensure the user's comfort.

The adhesive sealing capability of our novel light shields tends to diminish with use, and this may result in a shield having to be discarded while it is otherwise still usable. We have accordingly developed, and consider part of our invention, a novel accessory which restores the sealing capacity of the shield, thereby extending its service life.

This novel accessory includes an adhesively faced member configured to match the band of adhesive on the light shield. The accessory is attached to the light shield, and the adhesive of the accessory is then utilized to attach the resulting assembly to the user's face.

From the foregoing, it will be apparent to the reader that one primary object of our invention is the provision of a novel shield for blocking the transmission of light to the eyes of a subject using the shield.

Other important and related but more specific objects of our invention reside in the provision of light shields:

which can be employed in both human and other animal applications;

which are capable of blocking essentially all light from the user's eyes;

which, in conjunction with the preceding object, allow air to freely circulate to the user's eyes; are moisture and odor absorbent, soft, and pliable; and do not require straps, bands, or the like to hold the shield in place.

Yet another important, specific object of our invention, is the provision of light shields which are adhesively attachable to the user's face, thence keeping the shield from shifting during use, providing a light tight seal between the shield and the user's face, and contributing to the user's comfort.

Still another important, primary object of our invention resides in the provision of a novel, simple accessory that can be used in association with light shields embodying the principles of the present invention to extend the useful life of the latter.

And yet another important and primary object of our invention is the provision of novel methods for blocking the transmission of light to a subject's eyes which make use of light shields embodying the principles of the present invention.

Other important objects and features and additional objects of our invention will become apparent from the appended claims and as the ensuing detailed description and discussion proceeds in conjunction with the accompanying drawing, in which:

FIG. 1 is a plan view of a light shield embodying and constructed in accord with the principles of the present invention;

FIG. 2 is a section through the light shield taken substantially along line 2—2 of FIG. 1;

FIG. 3 is a view similar to FIG. 2 of a modified light shield construction;

FIG. 6 is a plan view of an accessory which is usable with the shield to extend its service life;

FIG. 7 is a section through the accessory taken substantially along line 7—7 of FIG. 6; and FIG. 8 is a partial section of the shield and accessory taken along lines corresponding to those on which FIGS. 2 and 7 were taken.

Figure 4:
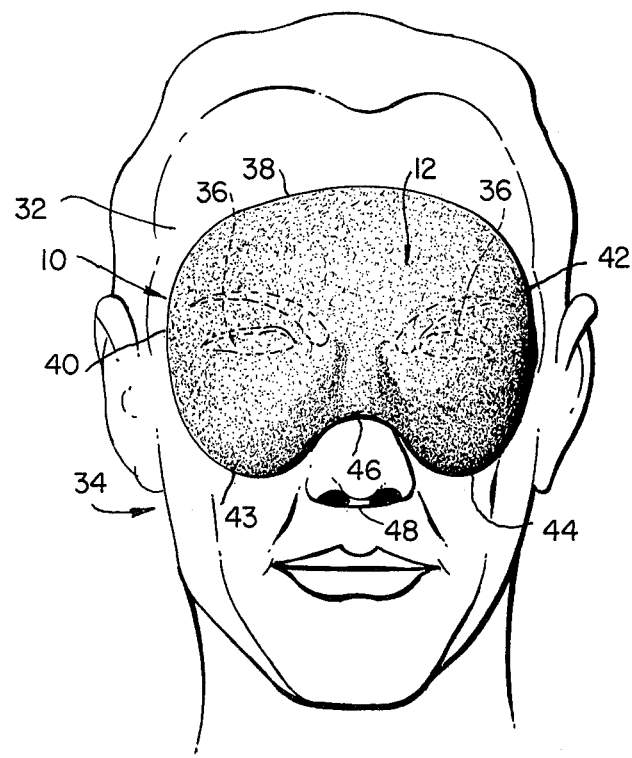
FIG. 4 is a full face view showing the light shield adhesively fixed in place on a subject's face.

Referring now to the drawing, FIGS. 1 and 2 depict a light shield 10 constructed in accord with and embodying the principles of the present invention.

Light shield 10 is composed of a mask 12 and a shield-to-subject attachment band 14. The latter extends around the periphery of and is fixed to the rear side 16 of mask 12.

The mask 12 of light shield 10 is designed to block the transmission of light to the user's eyes; to be soft and pliable; to absorb odors and moisture; and to allow air to circulate freely to that portion of the user's face covered by the light shield. It includes front and rear, microporous covers 18 and 19 joined around the periphery of the masking portion to contain a stratum of activated carbon 20 therebetween as shown in FIG. 2 or two microporous, carbon faced or impregnated sheets 21 and 22 in face-to-face relationship as in the mask 23 of the light shield 24 shown in FIG. 3. Appropriate materials of the last-mentioned character are the #2X-41A and #67-0A papers available from the Speciality Papers Division of Mead Corporation; the 40 point carbon impregnated paper produced by Barnebey-Cheney Company; and the one-eighth inch carbon impregnated paper and 20 point carbon impregnated felt available from Fiber Materials, Inc. Other materials may of course be employed as long as they have the necessary requisites of opacity, softness, pliability, and odor and moisture absorbency and are sufficiently porous or pervious to permit free circulation of air through the mask.

The attachment band fixed to the rear side 16 of mask 12 (or to the rear side of mask 23) and extending around its periphery will preferably be made from a double-coated adhesive tape of medical grade, especially in applications involving the use of a light shield by human subjects. 3-M Brand double-coated medical tapes #1512 and #1522 are satisfactory.

Exemplary band 14, thus fabricated, includes a backing member 25 faced on opposite sides with adhesive layers 26 and 28 overlaid with protective, peel away covers, only one of which (30) is shown (see FIG. 2).

Attachment band 14 is attached to mask 12 simply by peeling off the second of the protective strips to expose adhesive layer 26 and then pressing the band 14 against the rear side 16 of mask 12 to adhesively secure the band in place.

As shown pictorially in FIG. 1, protective strip 30 can subsequently be peeled away exposing adhesive layer 28 by which the light shield is attached to the face of the user.

Figure 5:
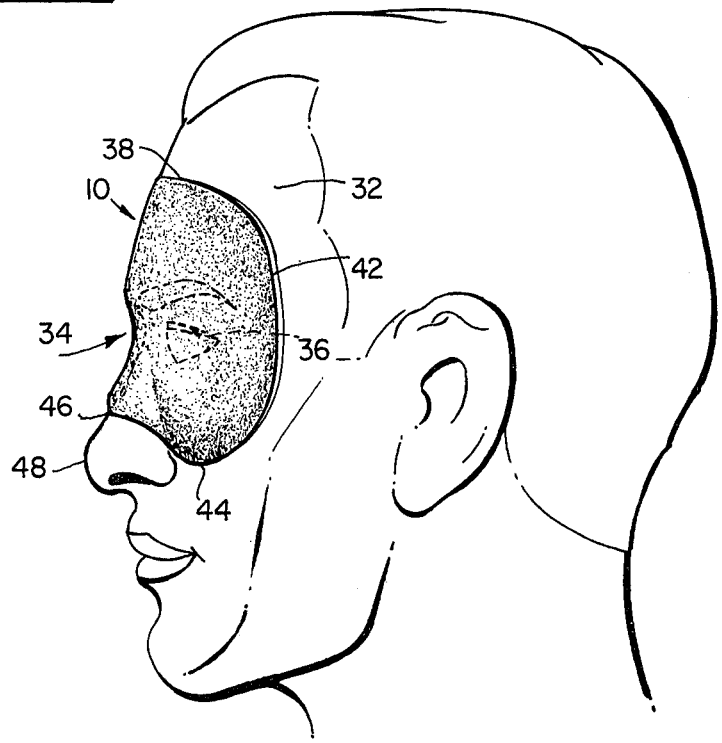
FIG. 5 is a profile of the subject's face with the shield secured in place.

FIGS. 4 and 5 show the light shield adhesively attached to the face 32 of a subject 34 to keep light from reaching his eyes 36.

As discussed above, the dimensioning and configuration of light shield 10 are important in keeping essentially all light from penetrating to the user's eyes through the soft tissues surrounding or overlying them. This is accomplished, in applications of our invention involving humans, by dimensioning and configuring the mask so that it will extend superiorly past the supraorbital margins and the superciliary arches to cover a portion of the forehead overlying the frontal bone as indicated by reference character 38. Laterally, as indicated by reference characters 40 and 42, the light shield extends past the frontal process of the zygomatic bone and over the anterior temporal fossa. Inferiorly, as shown by reference characters 43 and 44, the shield extends past the infraorbital margin and zygomatic arches to cover the upper portion of the maxilla. Finally, as indicated by reference character 46, the shield extends down over and covers all but the lower portion of the subject's nose 48. Typically, as indicated in the drawing, approximately the lower one-fourth of the nose will be exposed.

As is also shown in FIGS. 4 and 5, the novel construction of shield 10 permits it to conform closely to the contours of the subject's face. This ensures that continuous contact between the shield and the subject's face is made by ther peripheral band of adhesive 28, keeping light from penetrating at the edges of the shield. It also ensures that the shield does not shift during use even though it may be subjected to substantial forces as will occur, for example, when the user moves his face against a pillow while asleep.

As discussed above, the mask 12 of light shield 10 will typically remain serviceable well after adhesive layer 28 is no longer capable of maintaining the light tight seal we require. In this circumstance, the usefulness of shield 10 can be restored by making use of the accessory 50 discussed above and illustrated in FIGS. 6 and 7 of the drawing. Accessory 50, which is configured to match the adhesive layer 28 of shield 10, is fabricated of an adhesive layer tape, also preferably of medical grade, such as 3-M Brand medical tapes #1530 or #1530L. As shown in FIG. 6, accessory 50 has a backing member 52 faced with an adhesive layer 54 that is overlaid with a peel away protective strip 56.

Accessory 50 is used by pressing it against the rear side 16 of shield 10, thereby securing the accessory in place. The resulting shield-accessory assembly or unit is shown in FIG. 8.

Thereafter, the protective strip 56 is peeled away as shown pictorially in FIG. 6, exposing a fresh layer of adhesive (54) for attaching the shield to the user's face.

A still greater increase in service life can of course be obtained simply by continuing to add accessories as shown in FIGS. 6 and 7 to the shield by use of the technique just described.

Both the novel shield and accessory constructions discussed above lend themselves to economy of manufacture. Because of the anatomical features which must be covered by our novel light shields and the necessity of having them conform closely to the user's face, they are made in several sizes. As the attachment bands and accessories are, topologically, essentially identical in the different sizes, a set of the bands and accessories can be cut from one sheet of adhesive minimizing the generation of waste material.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent is:

1. The combination of a shield for blocking essentially all light from both of a human subject's eyes simultaneously while allowing fluid circulation to and from that portion of the subject's face covered by said shield, said shield comprising a masking means which is dimensioned and constructed to extend superiorly past the supraorbital margins and the superciliary arches of the subject's head to cover a portion of the forehead overlying the frontal bone, laterally past the frontal process of the zygomatic bone and over the anterior temporal fossa, interiorly past the infraorbital margin and zygomatic arches to cover the upper portion of the maxilla, and down over a major portion of the subject's nose, said masking means being pervious and opaque over the area it covers and being made of an odor and moisture absorbent material, and said shield also comprising a band of adhesive extending completely around the periphery of said masking means on one side thereof for securing the shield to the subject's face and for providing a seal between the shield and subject's face that will keep light from leaking therebetween to the subject's eyes, said strip of adhesive being a constituent of a double coated tape, said tape being secured to said mask around the periphery thereof and said tape further comprising a protective strip on the side thereof opposite said masking means which can be removed to expose an adhesive on said opposite side of said masking means, and an accessory for extending the useful life of said shield, said accessory comprising a flexible backing member configured to match said band of adhesive, a separate band of adhesive on said backing member, and a protective strip covering said adhesive, whereby said accessory can be attached to said light shield and the protective strip of said accessory then removed to expose said separate band of adhesive thereby making it available for attaching the light shield to the subject's face.

2. A light shield as defined in claim 1 wherein said masking means comprises front and back covers fabricated of a pliable, porous, sheet material and a layer of granular activated carbon between said covers.

3. A light shield as defined in claim 2 in which said front and back covers are joined together around the periphery of said masking means.

4. A light shield as defined in claim 1 wherein said masking means comprises at least one lamina of a porous, carbon faced or impregnated material.

* * * * *